(12) United States Patent
Mullen

(10) Patent No.: US 6,224,551 B1
(45) Date of Patent: May 1, 2001

(54) ULTRASOUND IMAGE DATA ARCHIVING AND COMMUNICATION TECHNIQUES

(75) Inventor: Paul Mullen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/224,449

(22) Filed: Dec. 31, 1998

(51) Int. Cl.[7] .................................................. A61B 8/00
(52) U.S. Cl. ........................................................ 600/437
(58) Field of Search ................................... 600/437, 443, 600/447; 395/601–615; 382/25, 26; 128/916

(56) References Cited

U.S. PATENT DOCUMENTS

| 4,958,283 | 9/1990 | Tawara et al. |
| 5,321,520 | 6/1994 | Inga et al. |
| 5,415,167 | * 5/1995 | Wilk ..................................... 600/407 |
| 5,513,101 | 4/1996 | Pinsky et al. |
| 5,603,323 | * 2/1997 | Pflugrath et al. ..................... 600/437 |
| 5,778,177 | * 7/1998 | Azar ................................ 395/200.32 |
| 5,851,186 | * 12/1998 | Wood et al. ......................... 600/437 |
| 5,944,659 | * 8/1999 | Flach et al. .......................... 600/300 |

FOREIGN PATENT DOCUMENTS 0 833 266 A2   9/1997 (EP).

OTHER PUBLICATIONS

"The Solution Isn't In The System It's In A Service", Wam!Net Medical, brochure, 1998.
"The One With The Smartest Data Wins", Informix, advertisement, The Wall Street Journal, Nov. 19, 1998.
Xin Li et al., *A World Wide Web Telemedicine System*, Spie vol. 2711, pp. 427–439, Dept. of Radiological Sciences, UCLA School of Medicine, Los Angeles, CA, 1996.

* cited by examiner

*Primary Examiner*—Marvin M. Lateef
*Assistant Examiner*—Ali M. Imam
(74) *Attorney, Agent, or Firm*—McAndrews, Held & Malloy, Ltd.

(57) ABSTRACT

Local storage of image data from ultrasound devices is transmitted through local controllers and through a network to a central controller which stores the data in a central data base storage device. The data may be retrieved by the local controllers by the use of separate passwords which are authenticated by central controller.

14 Claims, 1 Drawing Sheet

ULTRASOUND IMAGE DATA ARCHIVING AND COMMUNICATION TECHNIQUES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to ultrasound imaging systems, and more specifically relates to archiving of data generated by such systems.

Traditionally, ultrasound image data archiving and communication systems are hospital based. Each hospital maintains its own data base of ultrasound imaging data and maintains a local area network for distributing and retrieving such data. Maintaining such a data base is expensive for an individual hospital and requires trained personnel in order to operate the system efficiently and accurately. As a result, there is a need for a way of storing ultrasound image data in a more inexpensive manner which also enables rapid and secure retrieval of the data for an individual patient. This invention solves that need.

BRIEF SUMMARY OF THE INVENTION

This invention is useful in an archiving and communication system for ultrasound image data. The data is stored in a data base at a location remote from the locations at which the data is generated. The preferred embodiment includes generating ultrasound first image data at a first location, preferably by a first ultrasound imaging system. At least some of the first image data is stored at the first location, preferably by a first data base storage device. Second image data is generated at a second location different from the fist location, preferably by a second ultrasound imaging system. At least some of the second image data is stored at the second location, preferably by a second data base storage device. At least some of the first image data is transmitted from the first location to the data base at a third location different from the first location and the second location, preferably by a network. At least some of the second image data is transmitted from the second location to the database at the third location, preferably by the network. The first image data written to the data base at the third location is deleted from the first location, preferably by a first controller. The second image data written to the data base at the third location is deleted at the second location, preferably by a second controller. At least some of the first image data is read from the data base, preferably by a central controller. The first image data read from the data base is transmitted to the first location, preferably by the network. At least some of the second image data is read from the data base, preferably by the central controller. The second image data read from the data base is transmitted to the second location, preferably by the network.

By using these techniques, image data generated at the first and second locations can be stored in a data base at the third location and can be retrieved when needed. Thus, the efficiency and accuracy of the system is increased, while the cost is decreased.

DETAILED DESCRIPTION OF THE INVENTION

Figure 1:
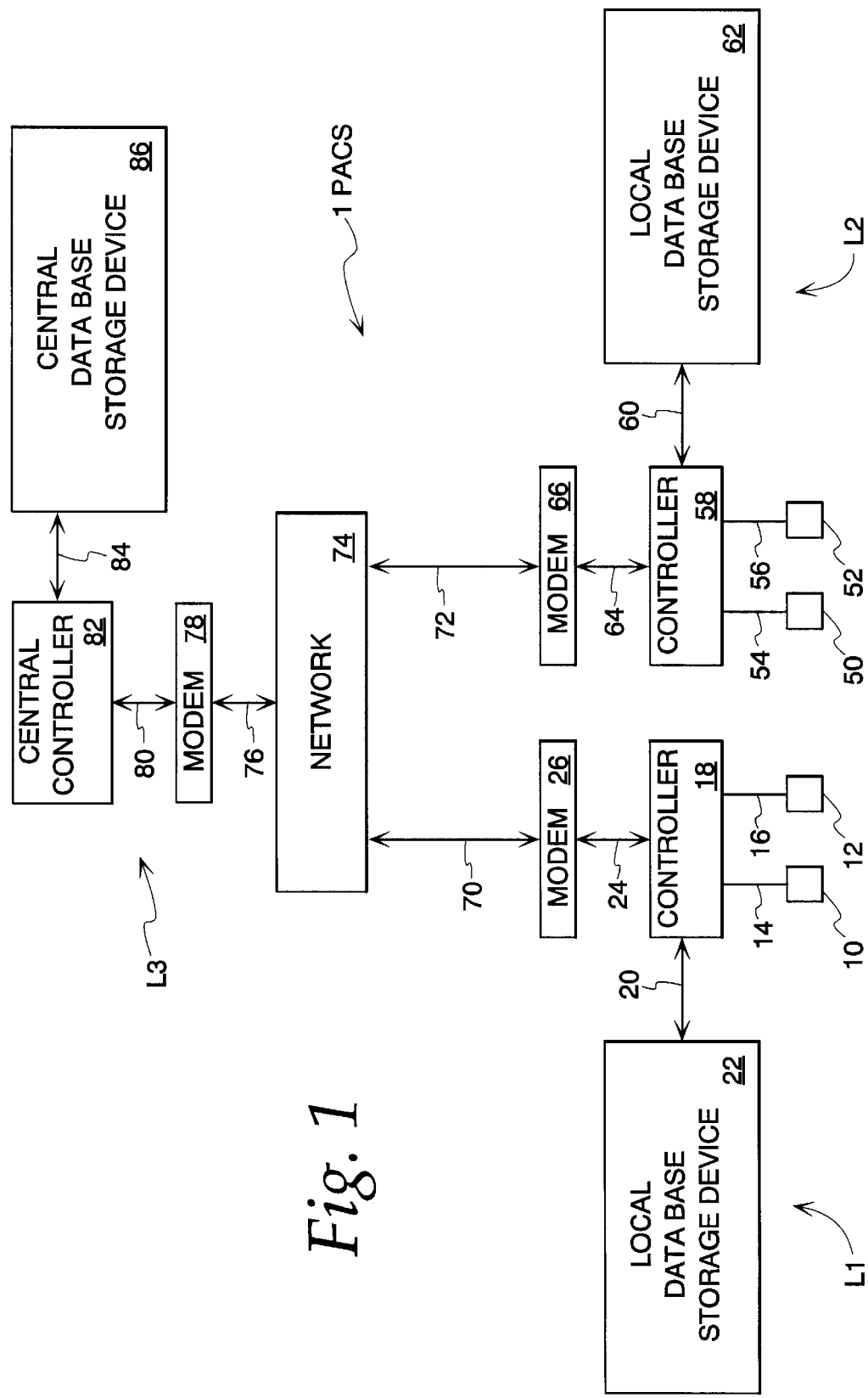
FIG. 1 is a schematic block diagram of a preferred form of archiving and communication system made in accordance with the preferred embodiment.

FIG. 1 illustrates an archiving and communication system 1 made in accordance with the preferred embodiment of the invention. Ultrasound imaging systems 10 and 12 scan subjects under study, such as patients, in a first location L1, such as a hospital, and provide image data over buses 14 and 16, respectively, to a controller 18 which may be a personal computer. The controller 18 is programmed in a well known manner to transmit the image data over a bus 20 to a local data base storage device 22 which may take the form of a variety of different types of memories, including tape drives and disc drives. Controller 18 includes a data base management program of a well known type in order to write the data to storage device 22 and read the data from storage device 22. Alternatively, device 22 may comprise the hard drive of the controller 18. Controller 18 transmits data from storage device 22 over bus 24 to a conventional telephone line modem 26.

At another location L2 which may be another hospital, an ultrasound imaging system 50 and another ultrasound imaging system 52 scan subjects under study, such as patients, in order to generate image data which is transmitted over buses 54 and 56, respectively, to a controller 58 which may be a personal computer. Controller 58 is programmed to receive the image data and transmit it over a bus 60 to a local data bus storage device 62. Device 62 may be the same type as device 22. Controller 58 is programmed in the same way as controller 18 and may transmit data from storage device 62 over a bus 64 to a modem 66. Modem 66 may be constructed like modem 26.

The image data from modems 26 and 66 are transmitted over conventional telephone lines 70 and 72, respectively, to a conventional communication network 74, such as a telephone network or the internet. Network 74 may transmit the image data asynchronously by using the Internet protocol. The network also may transmit image data synchronously by using ATM cells. The network includes a conventional telephone line 76 which transmits the image data through a conventional modem 78 and a bus 80 to a central controller 82. Central controller 82 executes a data base management program which is well known in the art to read image data from and write image data to a central data base storage device 86. The image data is transmitted from and to controllers 18 and 58 via network 74 and modems 26, 66 and 78. Device 86 may be constructed like device 22 or device 62, but has much larger capacity since it is receiving image data from several different locations. Modem 78, controller 82 and storage device 86 are located together in a third location L3 which is different from locations L1 and L2.

Modems 26, 66 and 78 are compatible with the telephone lines 70, 72, and 76. If the telephone lines are conventional, then the modems likewise are conventional devices which can modulate and demodulate data from analog to digital form as required. However, if the telephone lines are T1 lines or SONET lines, then the modems are made compatible with those types of communication lines.

After image data has been transmitted from either storage device 22 or storage device 62 and written into device 86, the corresponding data may be deleted from devices 22 or 62 in order to provide for storage of additional image data from ultrasound imaging systems 10, 12, 50 and 52.

In order for storage device 22 to receive data from storage device 86, controller 18 connects with central controller 82 through modem 26, network 74 and modem 78, and controller 18 then transmits a password to central controller 82.

Central controller 82 authenticates the password, and if it is authentic, controller 82 reads data for a specified patient as identified by controller 18 from storage device 86 and transmits the data back through the modems and network to controller 18. The retrieved image data then is stored in storage device 22.

Controller 58 may obtain image data from storage device 86 in the same manner as controller 18, and may store the retrieved image data in storage device 62 in the previously described manner. In order to retrieve image data from device 86, controller 18 transmits a first password, and controller 58 transmits a second password different from the first password. In this manner, the date retrieval remains secure. If desired, passwords also may be required to store image data in storage device 86.

By using the foregoing techniques, image data may be safely stored in a central location and retrieved by the use of passwords over a variety of networks in order to increase the efficiency, accuracy and security of the image data storage.

Those skilled in the art will recognize that various modifications and changes may be made in the preferred embodiment without departing from the true spirit and scope of the invention as defined in the accompanying claims.

What is claimed is:

1. A picture archiving and communication system for ultrasound image data comprising in combination:
    a first group of ultrasound imaging systems connected to generate first image data;
    a first data base storage device storing at a first location at least some of the first image data;
    a second group of ultrasound imaging systems connected to generate second image data;
    a second data base storage device storing at a second location at least some of the second image data;
    a central data base storage device connected to store at a third location the first image data and second image data;
    a central controller connected to read and write data to the central data base storage device;
    a network coupled to the central controller;
    a first controller connected to transmit the first image data between the first data base and the central controller over the network and thereafter to delete at least a portion of the first image data from the first data base storage device; and
    a second controller connected to transmit the second image data between the second data base and the central controller over the network and thereafter to delete at least a portion of the second image data from the second data base storage device, whereby the first and second image data can be archived on the central data base storage device while at least some of the first image data is deleted from the first data base storage device and at least some of the second image data is deleted from the second data base storage device.

2. Apparatus, as claimed in claim 1, wherein the central controller is programmed to require a first pass word from the first controller before allowing the transmission of image data to the first controller and to require a second pass word from the second controller before allowing the transmission of image data to the second controller.

3. Apparatus, as claimed in claim 1, wherein the network comprises an asynchronous networks.

4. Apparatus, as claimed in claim 3, wherein the network is connected to operate under the internet protocol.

5. Apparatus, as claimed in claim 1, wherein the network comprises a synchronous switching network.

6. Apparatus, as claimed in claim 5, wherein the network is connected to transport ATM cells.

7. Apparatus, as claimed in claim 1, wherein the first controller, second controller and central controller each comprises a modem.

8. Apparatus, as claimed in claim 1, wherein the first controller and second controller each comprise a personal computer.

9. In a picture archiving and communication system for ultrasound image data, a method of storing the data in a data base at a location remote from the locations at which the data is generated comprising the steps of:
    generating ultrasound first image data at a first location;
    storing at least some of the first image data at the first location;
    generating second image data at a second location different from the first location;
    storing at least some of the second image data at the second location;
    transmitting at least some of the first image data from the first location to the data base at a third location different from the first location and the second location;
    transmitting at least some of the second image data from the second location to the data base at the third location;
    deleting at the first location at least some of the first image data written to the data base at the third location;
    deleting at the second location at least some of the second image data written to the data base at the third location;
    reading at least some of the first image data from the data base;
    transmitting to the first location the first image data read from the data base;
    reading at least some of the second image data from the data base;
    transmitting to the second location the second image data read from the data base, whereby image data generated at the first and second locations can be stored in a data base at the third location and can be retrieved when needed.

10. A method, as claimed in claim 9, wherein the step of reading at least some of the first image data comprises the step of authenticating a first pass word transmitted from the first location and wherein the step of reading at least some of the second image data comprises the step of authenticating a second pass word transmitted from the second location.

11. A method, as claimed in claim 9, wherein the steps of transmitting each comprise the step of transmitting asynchronously.

12. A method, as claimed in claim 11, wherein the steps of transmitting each comprise the step of operating under the internet protocol.

13. A method, as claimed in claim 9, wherein the steps of transmitting each comprises the step of transmitting synchronously.

14. A method, as claimed in claim 13, wherein the steps of transmitting each comprises the step of sporting ATM cells.

* * * * *